United States Patent
Andersen et al.

(10) Patent No.: US 10,195,364 B2
(45) Date of Patent: Feb. 5, 2019

(54) GAS RELEASE CELL

(71) Applicant: L.O.M. Laboratories Inc., Vancouver (CA)

(72) Inventors: Allan Andersen, Johnston, IA (US); Lionel Stuart Matthews, Calgary (CA); Scott E. Castanon, Carlsbad, CA (US)

(73) Assignee: L.O.M. Laboratories Inc., Vancouver (CA)

( * ) Notice: Subject to any disclaimer, the term of this patent is extended or adjusted under 35 U.S.C. 154(b) by 148 days.

(21) Appl. No.: 15/128,930

(22) PCT Filed: Mar. 26, 2014

(86) PCT No.: PCT/IB2014/060187
§ 371 (c)(1),
(2) Date: Sep. 23, 2016

(87) PCT Pub. No.: WO2015/145207
PCT Pub. Date: Oct. 1, 2015

(65) Prior Publication Data
US 2017/0100548 A1    Apr. 13, 2017

(51) Int. Cl.
*A61M 5/32* (2006.01)
*B33Y 80/00* (2015.01)
(Continued)

(52) U.S. Cl.
CPC ........ *A61M 5/3234* (2013.01); *A61M 5/2053* (2013.01); *B33Y 80/00* (2014.12);
(Continued)

(58) Field of Classification Search
CPC .. A61M 5/155; A61M 5/2046; A61M 5/2053; A61M 5/3015; A61M 5/3148; A61M 5/3232; A61M 5/3234; A61M 2005/3241; A61M 2005/3242; A61M 2205/8218; A61M 2205/3225; A61M 2205/3231
See application file for complete search history.

(56) References Cited

U.S. PATENT DOCUMENTS 2,545,017 A * 3/1951 Billingsley ......... A61M 5/2053
604/143
3,527,212 A * 9/1970 Clark ..................... A61M 5/30
604/148

(Continued)

FOREIGN PATENT DOCUMENTS

EP    0479217 A1    4/1992
EP    2455125 A2    5/2012
(Continued)

*Primary Examiner* — Kami A Bosworth
(74) *Attorney, Agent, or Firm* — Oyen Wiggs Green & Mutala LLP

(57) ABSTRACT

A gas release cell for use with pneumatically actuated sharps-containing medical devices. The gas release cell has a rigid outer shell and a sealing membrane sealingly engaged with the rigid outer shell. A compressed propellant is retained within the gas release cell by the sealing membrane, and the sealing membrane is rupturable to actuate the medical device by releasing compressed propellant from the gas release cell.

20 Claims, 10 Drawing Sheets

(51) Int. Cl.
  *A61M 5/20*  (2006.01)
  *A61M 5/31*  (2006.01)

(52) U.S. Cl.
  CPC ............... *A61M 2005/312* (2013.01); *A61M 2205/8225* (2013.01); *A61M 2207/00* (2013.01)

(56) References Cited

U.S. PATENT DOCUMENTS

| | | | |
|---|---|---|---|
| 4,031,889 A * | 6/1977 | Pike | A61M 5/2053 |
| | | | 604/144 |
| 4,478,150 A | 10/1984 | Sayler | |
| 4,940,460 A | 7/1990 | Casey | |
| 5,398,850 A * | 3/1995 | Sancoff | A61M 5/14593 |
| | | | 222/386.5 |
| 5,623,975 A | 4/1997 | Simson | |
| 5,765,751 A | 6/1998 | Joshi | |
| 5,814,019 A * | 9/1998 | Steinbach | A61M 5/155 |
| | | | 604/131 |
| 5,868,713 A | 2/1999 | Klippenstein | |
| 6,047,865 A | 4/2000 | Shervington | |
| 6,406,461 B1 * | 6/2002 | Ellingsen | A61M 5/3232 |
| | | | 604/110 |
| 6,475,181 B1 | 11/2002 | Potter | |
| 7,156,257 B2 | 1/2007 | de la Serna | |
| 7,320,677 B2 | 1/2008 | Brouillette | |
| 7,654,983 B2 | 2/2010 | De La Serna | |
| 7,717,874 B2 | 5/2010 | Landau | |
| 7,811,259 B2 | 10/2010 | Klippenstein | |
| 2008/0293156 A1 * | 11/2008 | Smith | B01L 3/502 |
| | | | 436/174 |
| 2010/0204660 A1 * | 8/2010 | McKinnon | A61M 25/0606 |
| | | | 604/244 |
| 2010/0222739 A1 | 9/2010 | Klippenstein | |
| 2010/0263545 A1 | 10/2010 | Morgan | |
| 2012/0004621 A1 | 1/2012 | Shaw | |
| 2012/0073674 A1 | 3/2012 | Tatarek | |
| 2012/0118428 A1 * | 5/2012 | Steinbach | A61M 5/14276 |
| | | | 141/3 |

FOREIGN PATENT DOCUMENTS

| | | |
|---|---|---|
| FR | 2831448 B1 | 8/2005 |
| NL | 9000292 | 9/1991 |
| WO | 9104760 | 4/1991 |
| WO | 9834659 | 8/1998 |
| WO | 0002607 | 1/2000 |
| WO | 0144044 A1 | 6/2001 |
| WO | 03051435 A1 | 6/2003 |
| WO | 2006024172 A1 | 3/2006 |
| WO | 2011136731 A1 | 11/2011 |
| WO | 2012162821 A1 | 12/2012 |

* cited by examiner

GAS RELEASE CELL

REFERENCE TO RELATED APPLICATIONS

This application is a 371 of Patent Cooperation Treaty patent application No. PCT/IB2014/060187 filed 26 Mar. 2014, the entirety of which is incorporated by reference herein.

TECHNICAL FIELD

This application relates to a gas release cell for releasing compressed propellant. In some embodiments, the gas release cell is used to actuate a pneumatically-actuated retractable sharps-containing medical device such as a pneumatically-actuated retractable-needle syringe.

BACKGROUND

It is well known that many dangerous communicable diseases are spread through contacting the body fluids of an infected person. After use of a syringe, residual body fluids are likely to remain on or within the syringe needle. For this reason, syringes are typically intended for a single use only. In order to be handled safely after use, the needle of a syringe must be covered to prevent it from accidentally stabbing a person who is, for example, collecting the syringe for disposal, thereby releasing residual body fluids into such person. Typically, a protective cap is provided with the syringe, which after use of the syringe can be used to cover the tip of the needle. However, it sometimes happens that persons attempting to cap a used needle miss the cap and accidentally stab themselves, resulting in potential exposure to communicable diseases.

Accordingly, it is desirable to provide a syringe wherein the needle can be retracted into the syringe following use. Syringes including retractable needles wherein the retraction of the needle is accomplished by means of pneumatic actuation have been developed, as exemplified by U.S. Pat. No. 5,868,713 to Klippenstein and U.S. Pat. No. 7,811,259 to Klippenstein, both of which are incorporated by reference herein.

Syringes utilizing pneumatic actuation must have some mechanism for causing the pneumatic activation. In the syringe designs described in U.S. Pat. Nos. 5,868,713 and 7,811,259, the mechanism for causing the pneumatic activation is a gas release cell that contains a compressed propellant, and is ruptured at an appropriate point in time to release compressed propellant and retract the needle within the syringe. A design for gas release cells for use in such devices that can be reliably and rapidly manufactured in an automated, cost-effective manner and easily assembled into the finished device in an automated fashion has not heretofore been available.

There remains a need for gas release cells that can retain compressed propellant for release at a desired time, which can be reproducibly and rapidly manufactured, and/or which can be easily assembled into a finished medical device, including pneumatically actuated retractable-needle syringes such as those described in U.S. Pat. Nos. 5,868,713 and 7,811,259.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One example embodiment provides a gas release cell for use with a pneumatically-actuated sharps containing medical device. The gas release cell has an inner wall comprising a rigid material and defining an aperture through the gas release cell. An outer wall comprising a rigid material extends around the inner wall. A base is coupled to the inner and outer walls in sealing engagement therewith. A rupturable membrane is coupled to the inner and outer walls in sealing engagement therewith, so that the rupturable membrane, inner and outer walls and base define a sealed propellant chamber. A compressed propellant is contained within the propellant chamber.

In some embodiments, the gas release cell has surface features for preventing formation of a seal between the gas release cell and one or more adjacent components of a medical device in which the gas release cell is used. In some embodiments, the surface features are ribs, channels, or a component shape that is not complementary to the shape of a component of the medical device that contacts the gas release cell.

In some embodiments, the medical device is a pneumatically-actuated retractable-needle syringe.

In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

In this specification, "seals" or "sealingly engages" means that two elements are engaged with sufficient sealing capability that the function for which the sealing is provided can be effectively performed.

"Distal" means the direction towards the tip of the needle when the hypodermic syringe assembly is in the assembled state. "Proximal" means the direction opposite of distal, i.e. the direction away from the tip of the needle when the hypodermic syringe assembly is in the assembled state.

"Injection force" means a force that would typically be applied by a user to the plunger of a syringe to inject a medicament into a patient.

"Post-injection force" means a force that is applied to activate the gas-actuated retraction mechanism described below after a user has completed injection of the medicament. In some embodiments, the post-injection force is greater than the injection force.

"Loading force" means a force typically applied by a user when drawing medicament into a syringe in preparation for administering that medicament to a patient.

Although the invention is described with reference to an exemplary embodiment of pneumatically-actuated retractable-needle hypodermic needle and syringe (which may be used in medical, dental or veterinary applications), some embodiments of the invention have application in other devices where gas release cells may be used. For example, pneumatic retraction may also be used in sharps-containing medical devices such as blood collection syringe systems, intravenous syringe systems, pneumatically-actuated retractable scalpels, radiological syringes, spinal syringe systems, and the like. Some embodiments of gas release cells according to some embodiments of the present invention may be useful in such devices.

According to some embodiments, a gas release cell for use with pneumatically actuated sharps-containing medical devices is provided. The gas release cell has a rigid outer shell and a sealing membrane sealingly engaged with the rigid outer shell. A compressed propellant is retained within the gas release cell by the sealing membrane, and the sealing membrane is rupturable to actuate retraction of a retractable sharp in the sharps-containing medical device by releasing compressed propellant from the gas release cell.

Figure 1A:
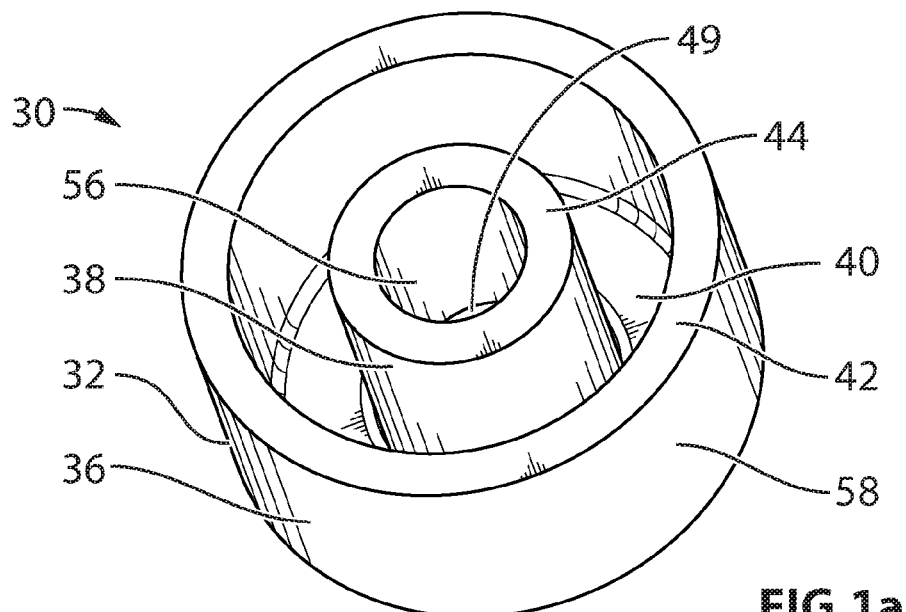
FIG. 1A shows a partial perspective view of a gas release cell according to one example embodiment in which the membrane has been omitted for clarity.
Figure 1B:
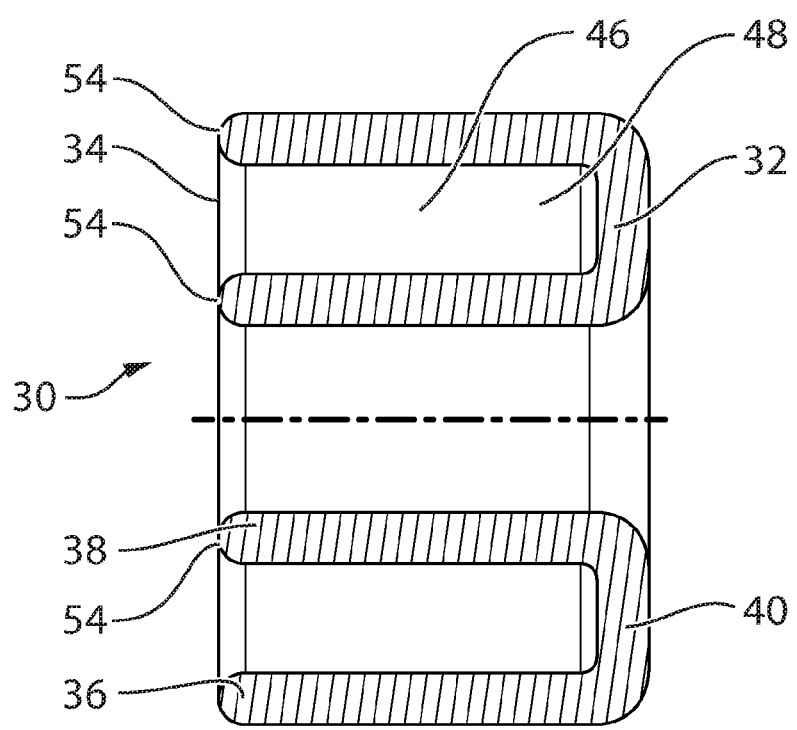
FIG. 1B shows a cross-sectional view of the gas release cell of FIG. 1.

With reference to FIGS. 1A and 1B, in one example embodiment a gas release cell 30 has a shell 32 and a sealing membrane 34 (not shown in FIG. 1A for clarity). Shell 32 is generally cylindrically shaped, having a generally cylindrical outer wall 36 and a generally cylindrical inner wall 38. In the illustrated embodiment, outer wall 36 and inner wall 38 are axially aligned. Outer wall 36 and inner wall 38 are connected at a first end by a base 40. In some embodiments, including the illustrated embodiment, outer wall 36, inner wall 38 and base 40 are integrally formed. In some embodiments, the outer wall 36, inner wall 38 and base 40 could be formed as separate elements and joined together in any suitable manner, for example by welding, use of suitable adhesives, or the like.

For clarity in the present description, the first end of gas release cell 30 defined by base 40 is described in a relative sense as the "bottom", and the end of gas release cell 30 opposite base 40 is described in a relative sense as the "top" for ease of reference to the drawings. However, it will be appreciated that gas release cell 30 can adopt any of a variety of different orientations, such that the "top" might be below the "bottom" in some orientations, and the use of these terms is not intended to be limiting to one specific orientation of gas release cell 30. For example, in the illustrated embodiment of FIG. 4, the exemplary gas release cell 134 is oriented with the top facing towards the base or distal end of the syringe 124.

At the top of gas release cell 30, an outer sealing edge 42 is defined by the upper edge of outer wall 36, and an inner sealing edge 44 is defined by the upper edge of inner wall 38.

Outer wall 36, inner wall 38, base 40 and membrane 34 define a sealed cavity 48 with a central aperture 49 extending through the gas release cell. Sealed cavity 48 contains the propellant 46 to be released by gas release cell 30.

Figure 2A:
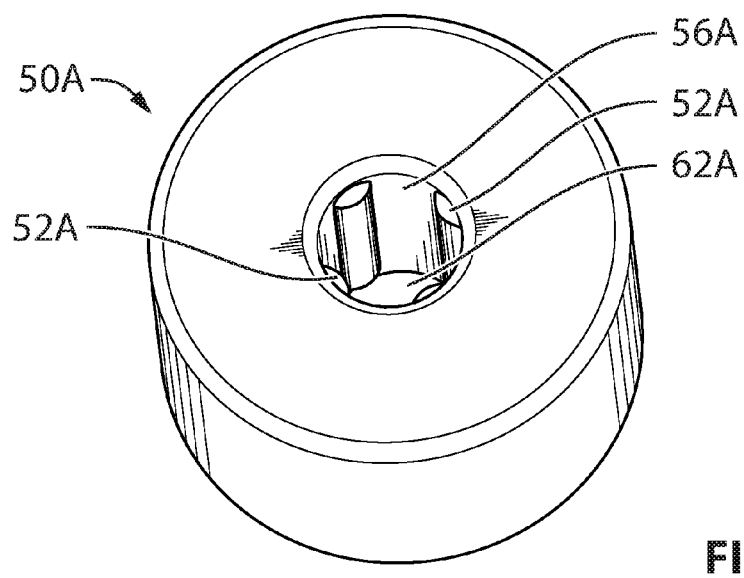
FIG. 2A shows a perspective view of a gas release cell according to a second example embodiment.

With reference to FIG. 2A, an alternative embodiment of a gas release cell 50A is illustrated. Gas release cell 50A is substantially similar to gas release cell 30 except for the presence of interior ribs 52A on the inner surface 56A of the inner wall of the gas release cell 50A. Ribs 52A extend in a generally axial direction within the inside circumference of the shell of gas release cell 50A as defined by inner surface 56A, and project radially inwardly from the inner surface 56A of the inner wall of gas release cell 50A. In some embodiments in which gas release cell 50A is used in a medical device, for example in the pneumatically-actuated retractable-needle syringe as described in greater detail below, ribs 52A can facilitate more reliable retraction of the needle by preventing the formation of a seal between the inner circumference of gas release cell 50A and other adjacent components of the syringe. That is, ribs 52A are surface features of gas release cell 50A configured to provide a gas passage between gas release cell 50A and one or more adjacent components of the medical device. The exact position and number of ribs 52A is not critical, so long as at least one rib is positioned in a manner that makes it difficult for the inner circumference of gas release cell 50A to form an airtight seal with at least one adjacent component of a pneumatically-actuated sharps-containing medical device. As an example, in the illustrated embodiment, ribs 52A can assist in preventing formation of an airtight seal between inner surface 56A and a generally cylindrical component of a medical device extending through central aperture 62A of gas release cell 50A.

Figure 2B:
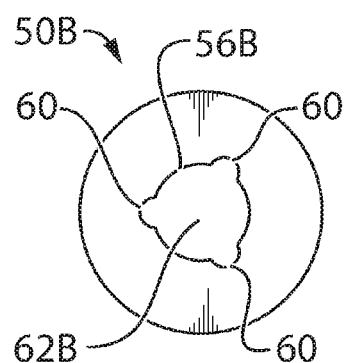
FIG. 2B shows a top view of a gas release cell according to a third example embodiment.

Other configurations of the surface of the gas release cell can be used to provide a gas passage between the gas release cell and other adjacent components of the sharps-containing medical device. For example, as illustrated in FIG. 2B, in an example embodiment of a gas release cell 50B, a plurality of channels 60 have been provided on the inner surface 56B of the inner wall of gas release cell 50B. Channels 60 extend generally axially through the inner surface 56B of the inner wall of gas release cell 50B. Channels 60 are configured to provide a gas passage between the gas release cell and other adjacent components of a medical device, by preventing formation of a seal between inner surface 56B and one or more adjacent components of a medical device. As an example, in the illustrated embodiment, channels 60 can assist in preventing the formation of an airtight seal between inner surface 56B and a generally cylindrical component of a medical device that extends through central aperture 62B of gas release cell 50B.

While in the illustrated embodiment three channels 60 have been shown spaced apart by approximately equal distances, the number and position of channels 60 could be varied and still provide a gas passage between the gas release cell and other components of a pneumatically-actuated sharps-containing medical device. In alternative embodiments, channels are provided on the outer surface of the outer wall of a gas release cell, or on both the inner and outer surfaces of the inner and outer walls, respectively, of the gas release cell, to prevent formation of an airtight seal between one or more components of a medical device in which the gas release cell is used.

Figure 2C:
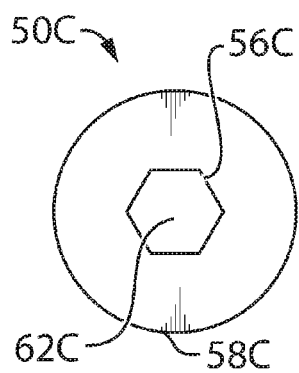
FIG. 2C shows a top view of a gas release cell according to a fourth example embodiment.

With reference to FIG. 2C, a further alternative embodiment of a gas release cell 50C is illustrated. Gas release cell 50C has an inner surface 56C with a shape that does not form a sealing engagement with an adjacent generally cylindrical component of a medical device extending through the central aperture 62C of the gas release cell 50C. In the illustrated embodiment, inner surface 56C is provided with a generally hexagonal cross-sectional shape. The generally hexagonal cross-sectional shape does not form a seal with a generally cylindrical component of a medical device inserted through the central aperture 62C of gas release cell 50C. Inner surface 56C could alternatively be provided with other shapes that do not form a seal with a generally cylindrical component of a medical device inserted through the central aperture 62C of gas release cell 50C, for example, inner surface 56C could be provided with an asymmetrical cross-section; a triangular, square, pentagonal or other polygonal shaped cross-section; a pear-shaped cross-section; an oval cross-section and so on. Any cross-sectional shape that facilitates formation of a gas passage between the inner surface of gas release cell 50C and a component of a medical device inserted through central aperture 62C of gas release cell 50C could be used.

The shape of inner surface 56C can be selected to be a shape that does not form a sealing engagement with other components of a pneumatically-actuated sharps-containing medical device in which gas release cell 50C is used based on the shape of a component to be inserted through the central aperture 62C of gas release cell 50C. For example, if the component to be inserted through the central aperture 62C of gas release cell 50C has a generally square cross-section, then the cross-sectional shape of inner surface 56C should be selected to be a shape other than a square, to provide a gas passage between gas release cell 50C and the components of the medical device in which it is used.

In alternative embodiments, the shape of the outer surface 58C of the gas release cell could be modified in a similar manner to that described for inside surface 56C, so that outer surface 58C does not form an airtight seal with one or more adjacent components of a pneumatically-actuated sharps-containing medical device in which the gas release cell is used. For example, in an embodiment in which the gas release cell sits within a generally cylindrical component of a medical device (e.g. the barrel of a syringe), the outer surface of the gas release cell could be provided with a generally hexagonal or other cross-sectional shape (e.g. an asymmetrical cross-section; a triangular, square, pentagonal or other polygonal shaped cross-section; a pear-shaped cross-section; an oval cross-section; and so on), so that the outer surface of the gas release cell does not form an airtight seal with the cylindrical component of the medical device. In some embodiments, the cross-sectional shape of both the inner surface and the outer surface of the gas release cell could be modified as described above to prevent formation of an airtight seal between the gas release cell and one or more adjacent components of a medical device.

Figure 2D:
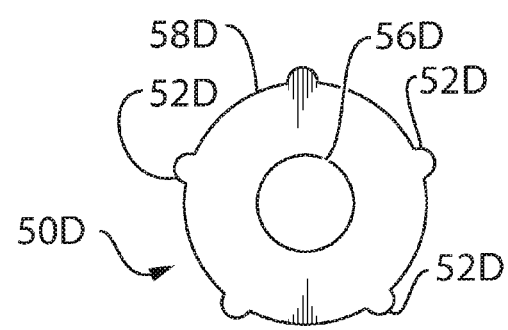
FIG. 2D shows a top view of a gas release cell according to a fifth example embodiment.

In some alternative embodiments, as illustrated with respect to an example gas release cell 50D in FIG. 2D, axially extending radially outwardly projecting ribs 52D analogous to ribs 52A are provided on the outer surface 58D of the outside circumference of the gas release cell to prevent formation of a seal between the gas release cell and one or more adjacent components of a pneumatically-actuated sharps-containing medical device. While in the illustrated embodiment five ribs 52D that are approximately symmetrically distributed about the outer surface 58D of gas release cell 50D have been illustrated, the number, distribution and configuration of ribs 52D could be varied, so long as ribs 52D are configured to provide a gas passage between gas release cell 50D and one or more components of a medical device. For example, gas release cell 50D could be used within a cylindrical barrel of a pneumatically-actuated sharps-containing medical device to prevent formation of a sealing engagement between the outer surface 58D of gas release cell 50D and the inner surface of the cylindrical barrel. In the illustrated embodiment, the inner surface 56D of gas release cell 50D is smoothly curved and circular in shape. In some embodiments, ribs 52A, 52D are provided on both the inside and outside circumferences of the same gas release cell to prevent formation of a seal between the gas release cell and one or more components of a pneumatically-actuated sharps-containing medical device.

Figure 2E:
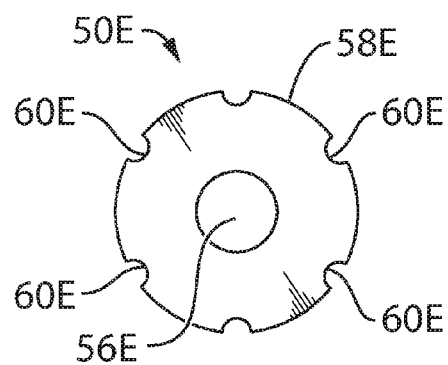
FIG. 2E shows a top view of a gas release cell according to a sixth example embodiment.

In some alternative embodiments, for example as illustrated with respect to an example gas release cell 50E in FIG. 2E, axially extending channels analogous to channels 60 of gas release cell 50B are provided on the outer surface 58E of the outside circumference of the gas release cell to prevent formation of a seal between the gas release cell and one or more adjacent components of a pneumatically-actuated sharps-containing medical device. While in the illustrated embodiment six channels 60E that are approximately symmetrically distributed around the outer surface 58E of gas release cell 50E have been illustrated, the number, distribution and orientation of channels 60E could be varied, so long as channels 60E are configured to provide a gas passage between gas release cell 50E and one or more components of a pneumatically-actuated sharps-containing medical device.

In some alternative embodiments, surface features that prevent formation of a sealing engagement between the gas release cell and one or more adjacent components of a pneumatically-actuated sharps-containing medical device are provided on multiple surfaces of the gas release cell. For example, in some embodiments, such features can be provided on both the inside and outside surfaces of the gas release cell. For example, in some embodiments, the features of any or all of FIG. 2A, 2B, 2C, 2D, 2E or 2F could be combined in any number of different permutations.

Figure 2F:
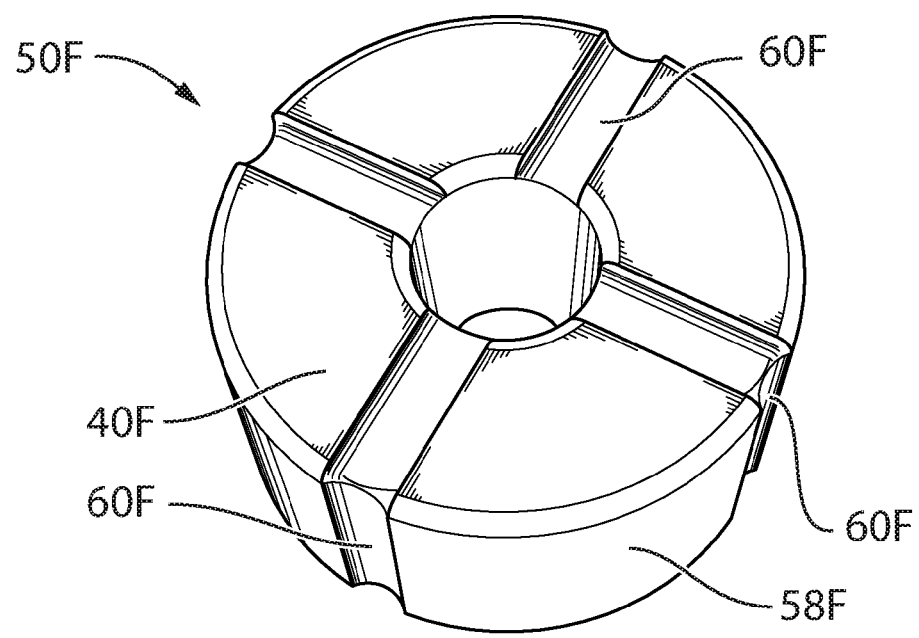
FIG. 2F shows a perspective view of a gas release cell according to a seventh example embodiment.

In some alternative embodiments, surface features that prevent formation of a sealing engagement between the gas release cell and one or more adjacent components of a pneumatically-actuated sharps-containing medical device are provided on the base 40 of the gas release cell. For example, as illustrated in FIG. 2F, channels 60F are provided on the outside surface 58F of gas release cell 50F, and channels 60F extend through the base 40F of gas release cell 50F. Such an example gas release cell 60F could potentially be used, for example, in a pneumatically-actuated retractable syringe as illustrated in FIGS. 3-9, in which the gas release cell could potentially form a sealing engagement with two components of the syringe, in this example embodiment the interior surface of the syringe barrel (144) and the engagement ring (160), as described in greater detail below. While an example embodiment having four channels 60F has been illustrated, the number and position of channels 60F could be varied to be provided in any shape, size or number, so long as channels 60F can provide a gas passageway between gas release cell 50F and one or more adjacent components of a pneumatically-actuated sharps-containing medical device.

While exemplary embodiments have been described in which the gas release cell is provided with surface features that can be used to prevent formation of an airtight seal between the gas release cell and one or more adjacent components of a pneumatically-actuated sharps-containing medical device, in alternative embodiments, surface features could be provided on one or more components of a medical device that are adjacent a gas release cell to prevent formation of an airtight seal between the gas release cell and the one or more adjacent components of the medical device.

In some embodiments, for example as illustrated in FIG. 1A, no surface features are provided on the gas release cell for preventing formation of a seal between the gas release cell and one or more adjacent components of a pneumatically-actuated sharps-containing medical device. For example, as illustrated in FIG. 1A, the inner surface 56 of the inner wall and the outer surface 58 of the outer wall are generally smooth and of symmetrical cross-sectional shape (circular in the illustrated embodiment). In some such embodiments, the dimensions of the gas release cell and/or of the components of the medical device are selected to allow sufficient tolerance that formation of a complete seal between the gas release cell and one or more components of the medical device is unlikely.

As best seen in FIG. 1B, in some embodiments, the top surfaces of inner and outer sealing edges 44, 42 are provided with a curved radius 54. In some embodiments, curved radius 54 facilitates coupling of shell 32 and sealing membrane 34, including for example in embodiments in which sealing membrane 34 is sealed to shell 32 using a thermal or heat sealing process. In some embodiments, the top surfaces of inner and outer sealing edges 42, 44 comprise a flat surface.

Gas release cell 30 and gas release cell 50 can be made from any suitable materials. In one example embodiment, at least outer wall 36 and inner wall 38 of shell 32 are made from a rigid material. In some embodiments, the rigid material is a suitable polymer, homopolymer or co-polymer, for example, polypropylene, polyethylene, high density polyethylene (HDPE), polyethylene terephthalate, polystyrene, polycarbonate, acrylic, polyvinyl chloride, polyester, a polyamide such as nylon, or the like. In some embodiments, shell 32 is made from laminated layers of two or more of the foregoing materials. In some embodiments, shell 32 is made from laminated layers of a suitable polymer, homopolymer or copolymer, or multiple layers thereof, and a metal foil, for example, aluminum foil. In some embodiments, use of a rigid material to form at least outer and inner walls 36, 38 of shell 32 assists in the reliable rupture of sealing membrane 34 when the gas release cell is in use.

In some embodiments, the material(s) used to manufacture gas release cell 30 or gas release cell 50 are selected for their biocompatibility and/or compliance with regulatory requirements. For example, in some jurisdictions, polyvinyl chloride, or plasticizers or phthalates incorporated into a polymer, are believed to be carcinogenic, and therefore the use of such materials in embodiments intended for use with a medical device may be restricted.

Shell 32 of the gas release cell can be formed in any suitable manner, for example extrusion, injection molding, compression molding, or the like. In some embodiments, shell 32 of the gas release cell is formed by injection molding. In some embodiments, shell 32 of the gas release cell could be formed by additive manufacturing processes such as 3D-printing.

The thickness of shell 32 can be selected based on the volume and intended use of the gas release cell (for example, considering the desired shelf-life of gas cell 30, and/or the anticipated pressures and temperatures to which gas cell 30 is expected to be subjected, and/or the amount of propellant to be contained within gas cell 30 to exert a desired retraction force or the like). In some embodiments intended for use in a pneumatically-actuated retractable-needle syringe having a volume of 3 cc in which gas release cell 30 has a volume in the range of 50 mm$^3$ to 175 mm$^3$, or any value therebetween, e.g. 75, 100, 125 or 150 mm$^3$, shell 32 has a thickness in the range of 0.30 to 0.70 mm, or any value therebetween, e.g. 0.40, 0.50 or 0.60 mm. In one example embodiment intended for use with a pneumatically-actuated retractable-needle syringe having a volume of 3 cc, the gas release cell has an overall diameter of approximately 7.5 mm. The dimensions provided herein are exemplary only, and are not intended to be limiting.

The materials selected to manufacture sealing membrane 34 and shell 32 should be selected so that membrane 34 can be sealingly secured to shell 32 to provide sealed cavity 48. In some embodiments, the sealing membrane 34 is made, in whole or in part, from the same material as shell 32. In some embodiments, sealing membrane 34 is made from a different material than shell 32, but the different material is selected so that it can still be securely adhered to shell 32.

In some embodiments, sealing membrane 34 is made from any suitable polymer, homopolymer or co-polymer, or multiple layers thereof, for example, polypropylene, polyethylene, high density polyethylene (HDPE), polyethylene terephthalate, polystyrene, acrylic, polyvinyl chloride, polyester, a polyamide such as nylon, or the like. In some embodiments, sealing membrane 34 is made in any suitable manner, for example by extrusion or co-extrusion. In some embodiments, sealing membrane 34 is any suitable multilayer film. In some embodiments, sealing membrane 34 is made from a laminated polymer-foil using a polymer, homopolymer or co-polymer, or multiple layers thereof, laminated with a metal foil. In some embodiments, the metal foil is aluminum foil. In some embodiments, sealing membrane 34 is made from any suitable laminate comprising a polymer, homopolymer or co-polymer. In some embodiments, sealing membrane 34 may be sprayed with a microthin polymer coating (for example, polyester or nylon), to provide desired properties to sealing membrane 34. For example, in some embodiments, the metal foil is sprayed with a polyester or other suitable polymer coating to enhance the abrasion resistance of the metal foil.

In some embodiments, use of a multilayer film for sealing membrane 34 enables the use of a thinner membrane than would be used if sealing membrane 34 comprised only a single layer of film. Without being bound by theory, use of a multilayer film can increase the tensile strength of the sealing membrane, which may increase the resistance of the sealing membrane to rupturing, for example due to forces applied by compressed gas contained within the gas release cell. In some embodiments, at least one layer of the multilayer film is selected for its ability to act as a migration barrier, i.e. as a barrier to the passage of moisture, gas and/or compressed propellant through the membrane, which may enhance retention of compressed propellant in the gas release cell (e.g. to extend the shelf life of the gas release cell).

In some embodiments, sealing membrane 34 is made from a laminated polymer-foil using a polymer, homopolymer or co-polymer, or multiple layers thereof, and shell 32 is made from the same polymer, homopolymer or co-polymer as is used in sealing membrane 34.

The thickness of sealing membrane 34 should be selected to be suitable for a given application, for example, to be sufficiently thick to allow propellant 46 to be captured and contained within the gas release cell during manufacture and storage, but sufficiently thin to permit sealing membrane 34 to be ruptured to release propellant 46 when in use. In some embodiments intended for use in a pneumatically-actuated retractable-needle syringe wherein the gas release cell has a volume in the range of about 50 mm$^3$ to 175 mm$^3$, including any value therebetween, e.g. 75, 100, 125 or 150 mm$^3$, the thickness of sealing membrane is in the range of 0.05 mm to 0.15 mm, including any value therebetween, e.g. 0.06, 0.07, 0.08, 0.09, 0.10, 0.11, 0.12, 0.13 or 0.14 mm.

In some embodiments, sealing membrane 34 is adhered to shell 32 after propellant 46 has been placed in the cavity defined inside shell 32 to form sealed cavity 48. In some embodiments, propellant 46 is placed in the cavity defined inside shell 32 in a liquid state, and sealed cavity 48 is formed by placing sealing membrane 34 over shell 32 containing liquid propellant 46 and adhering sealing membrane 34 to shell 32.

Sealing membrane 34 can be adhered to shell 32 in any suitable manner, for example through the use of suitable adhesives, including adhesives activated by ultraviolet (UV) or other light sources, by solvent welding, or through a thermal or heat sealing process such as direct contact or impulse sealing, ultrasonic welding, laser welding, radiofrequency (RF) welding (also called dielectrical sealing or high frequency welding), or one or more methods of heat sealing or adhesives in combination with mechanical sealing, or the like. In some embodiments, sealing membrane 34 is adhered to shell 32 using ultrasonic welding. In some embodiments, a method of heat sealing is used in combination with mechanical force to adhere sealing membrane 34 to shell 32. In some embodiments, adhesives in combination with mechanical force are used to adhere sealing membrane 34 to shell 32.

The propellant 46 used in the gas release cell should be selected to have properties suited to the range of conditions and uses to which the gas release cell will be exposed. Characteristics used to select a suitable propellant 46 may include one or more of: the ability of the propellant to voluminously expand when the sealing membrane of the gas release cell is punctured, low toxicity, biocompatibility, and the like. In one embodiment, propellant 46 is selected so as to be compressible to a liquid state, and to remain in a liquid state, within the gas release cell under an expected range of operating and storage conditions (e.g. −5° C. to 50° C. or any value therebetween, e.g. 0, 5, 10, 15, 20, 25, 30, 35, 40 or 45° C., and standard atmospheric pressure, e.g. approximately 760 mm Hg absolute pressure prevailing in the environment outside the gas release cell, although standard atmospheric pressure can vary with weather and elevation, and might reasonably be expected to range between 730 mm Hg to 790 mm Hg or any value therebetween, e.g. 740, 750, 760, 770 or 780 mm Hg under normal conditions). Propellant 46 expands into a gaseous state, thereby producing a pneumatic force when the gas release cell is ruptured. An example of a propellant 46 that is used in some embodiments of a gas release cell is a pharmaceutical-grade hydrofluorocarbon such as 1,1,1,2-tetrafluoroethane. In some other embodiments, medical grade nitrogen may be used to provide propellant 46. In some embodiments, carbon dioxide ($CO_2$) may be used to provide propellant 46.

In one example embodiment intended for use in a pneumatically-activated retractable-needle syringe, the gas release cell has a volume of approximately 125 mm$^3$, and holds approximately 0.1 mL (approximately 0.1 g) of propellant.

Figure 3:
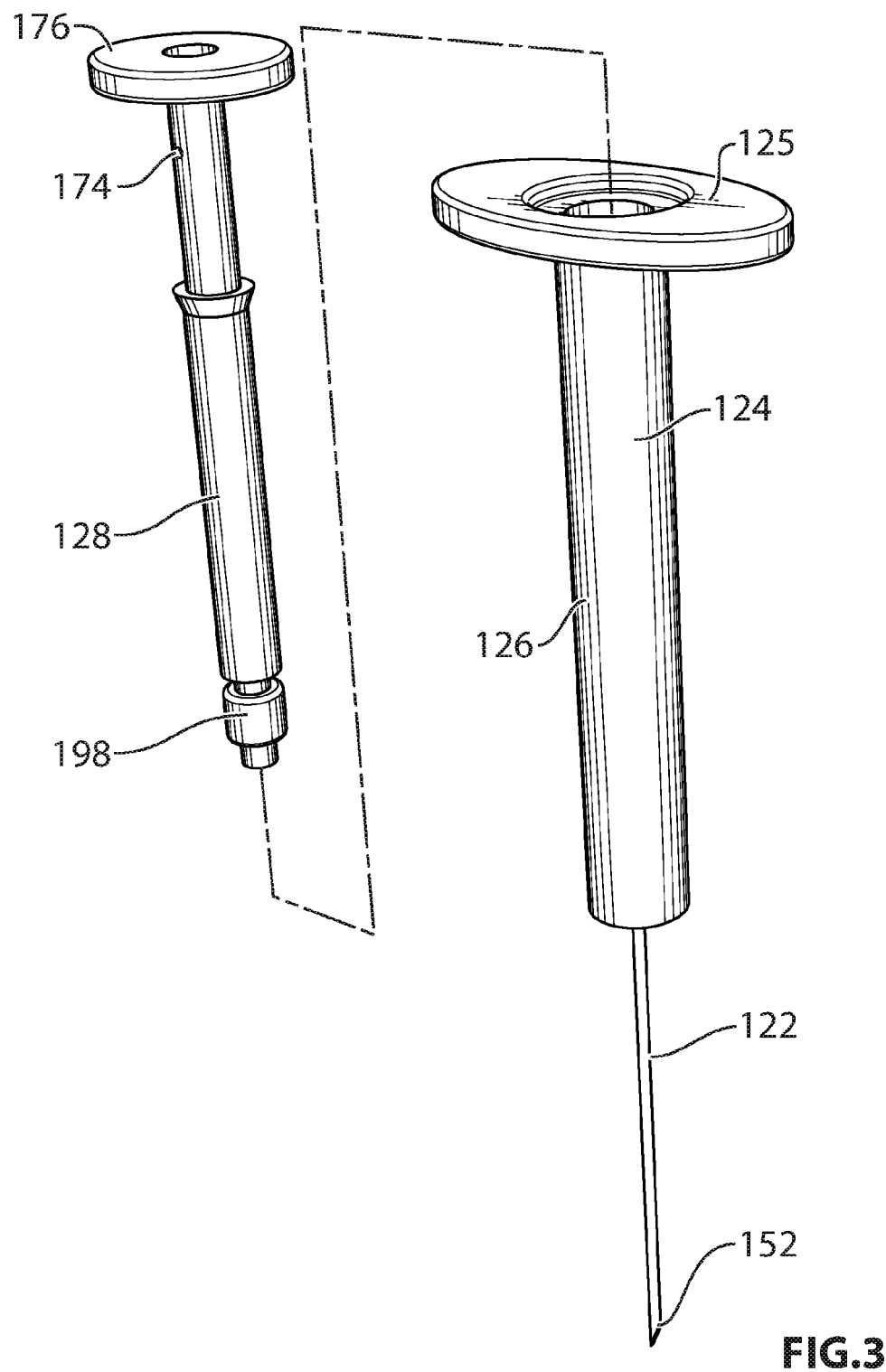
FIG. 3 shows an example embodiment of a pneumatically-actuated retractable-needle syringe incorporating a gas release cell according to one example embodiment.
Figure 4:
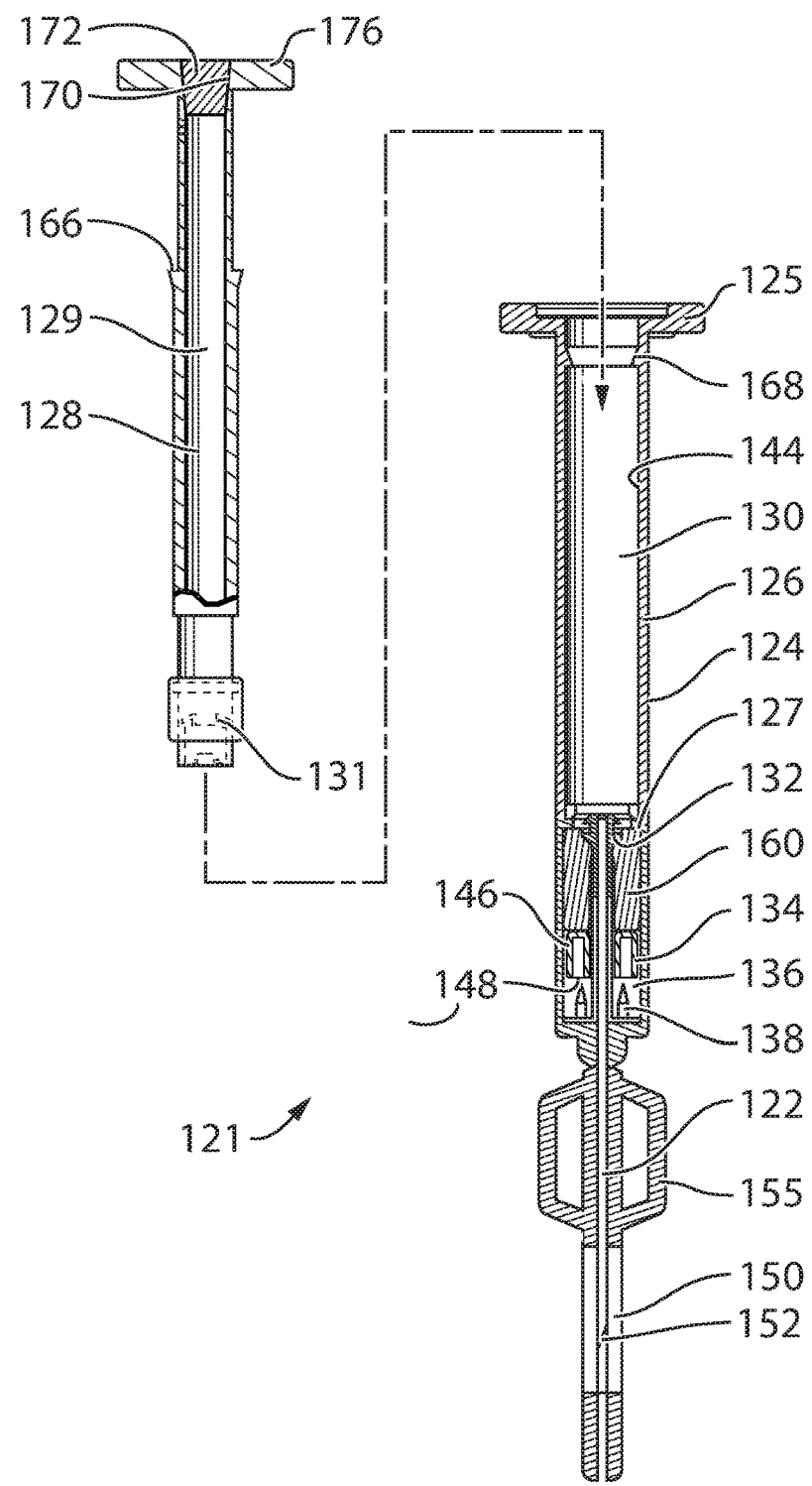
FIG. 4 shows a partial cross-sectional view of the syringe of FIG. 3.

With reference to FIG. 3, in one embodiment of a pneumatically-activated retractable-needle syringe incorporating an example embodiment of a gas release cell, a hypodermic needle 122 may be coupled to a syringe 124 for use in administration of a medicament to a patient using a plunger 128. As shown in FIG. 4, syringe 124 has a barrel 126, a plunger 128 slidingly and sealingly engageable within the barrel 126, and a retractable needle 122. The overall assembly of syringe 124, plunger 128 and needle 122 provides a syringe assembly 121.

A medicament chamber 130 is defined between retractable needle 122, the distal end of plunger 128 and an interior surface 144 of syringe barrel 126 for containing the medicament to be administered to the subject. Medicament chamber 130 is in fluid communication with needle 122 when syringe assembly 121 is in the assembled configuration, and plunger 128 is sealingly and slideably engaged within barrel 126 to move fluid within medicament chamber 130 through needle 122.

A gas release cell 134 is provided within barrel 126 within a gas release chamber 136, and a rupturing mechanism 138 for rupturing gas release cell 134 upon application of a post-injection force by a user is provided. In some embodiments, rupturing mechanism 138 is provided within gas release chamber 136.

In some embodiments of the present invention, including the illustrated embodiment, the plunger may be locked at or near the distal-most point of its travel and the needle is received within the plunger. With reference to FIG. 4, to facilitate needle retraction in this manner, plunger 128 includes a retraction lumen 129 therewithin for receiving needle 122 when needle 122 is retracted and a needle port seal 131 at a distal end of plunger 128 for assisting in the retraction of needle 122 by engaging with a needle header 132 in the manner described below.

Syringe 124 preferably includes a flange 125 formed therewith or attached thereto to facilitate grasping and usage of syringe assembly 121 by a user. Flange 125 may be provided at or near the proximal end of syringe 124. Flange 125 may be any suitable shape, for example a generally circular extension projecting radially outwardly from the barrel of syringe 124 or a pair of opposed projecting tabs serving as finger grips to facilitate manipulation of syringe 124 relative to plunger 128 by a user.

In some embodiments, including the illustrated embodiment, syringe 124 includes an internal radial wall 127 therein (FIG. 4). Internal radial wall 127 is provided towards the distal end of syringe 124 to stop movement of plunger 128 after injection of medicament into a subject in the manner described below.

Needle 122 projects from the distal end of syringe 124 and the hollow interior of needle 122 is in fluid communication with medicament chamber 130. Needle 122 is securely but releasably retained by a needle header 132 so that needle 122 is securely retained in place when syringe assembly 121 is in normal use, i.e. during loading of medicament into medicament chamber 130 and during injection of medicament into a subject. Needle 122 is releasable (via release of needle header 132 as described below) in response to force applied by the rupture of gas release cell 134 so that needle 122 can be retracted into the body of syringe 124 upon the application of a post-injection force by a user, as described below.

In some embodiments, a needle cover 150 is provided to cover needle 122 prior to use. Needle cover 150 may be laminated, cemented or otherwise affixed to the distal portion of syringe barrel 126 to secure it in place prior to use. Needle cover 150 can be twisted off or otherwise removed in any suitable manner to expose needle 122 for use. In some embodiments, needle cover 150 includes radially extending tabs 155 or other surface features to facilitate removal of needle cover 150.

In the illustrated embodiment, needle 122 is releasably retained in its initial position via needle header 132, as described below. Needle header 132 is provided at or near the proximal end of needle 122. Needle header 132 may be formed integrally with or separately from needle 122. In some embodiments, needle 122 may be crimped in, cemented to, or otherwise securely fixed to needle header 132. Needle header 132 securely retains needle 122 in place against the distally applied injection force of medicament being injected into a patient or against a proximal loading force when medicament is drawn into medicament chamber 130, but is releasable in the proximal direction in response to pressure produced by the release of a propellant from a gas release cell 134 as described below.

In the illustrated embodiment, needle header 132 engages with needle port seal 131 (provided in the distal tip of plunger 128 as described below) on or shortly before the application of a post-injection force by a user. Needle header 132 and/or needle port seal 131 provide a distal bearing surface for the application of proximally directed force created by gas pressure upon rupture of gas release cell 134. Needle port seal 131, alone or in combination with needle header 132, acts as a needle carrier to pull needle 122 into retraction lumen 129 through the force applied by compressed propellant released from gas release cell 134.

Needle 122 is hollow and has a downstream tip 152 for injection of medicament into a subject and an upstream intake opening 154 (FIG. 5) for receiving medicament from medicament chamber 130. In some embodiments, a needle membrane 156 (FIG. 5) is provided to cover the distal end of syringe 124. In some embodiments, needle membrane 156 more tightly seals gas release chamber 136 by sealingly engaging against needle 122. In some embodiments, needle membrane 156 is secured to the base 182 of perforator assembly 180 in any suitable manner, for example by suitable adhesives. In some embodiments, needle membrane 156 may assist in retaining needle 122 within syringe 124 once needle 122 has been retracted by providing a barrier to needle re-emergence. In some embodiments, needle membrane 156 may help to prevent any medicament from dripping off the end of needle 122 and into the surrounding environment after use.

Needle membrane 156 may be made of a soft, flexible material. In some embodiments, needle membrane 156 is made from silicon or rubber. In some embodiments, needle membrane 156 is made from a soft surgical-grade rubber or silicon such that, when needle 122 is retracted, needle membrane 156 tends to flow into itself and seal the hole left by needle 122. In some embodiments, needle membrane 156 is formed with a small, slightly conical hole that has a taper of approximately 30° relative to the longitudinal axis of syringe 124 positioned just at the point where needle 122 passes through needle membrane 156.

With particular reference to FIG. 4, a gas release cell 134 is contained within syringe barrel 126 distally of needle header 132, within gas release chamber 136. In the illustrated embodiment, gas release chamber 136 is defined between the distal tip of syringe barrel 126 and needle header 132. Depending on the configuration of the components of syringe assembly 121, the gas release chamber 136 could be defined between other components of the assembly. For example, in embodiments in which perforator assembly 180 described below is sealingly engaged by perforator mount 186 (FIG. 6) at the distal end of syringe barrel 126, gas release chamber 136 may be defined between the interior surfaces of the distal portion of syringe barrel 126, the needle header 132, and the base 182 of perforator assembly 180.

Gas release cell 134 has a shell 146 and a sealing membrane 148. Gas release cell 134 is oriented within gas release chamber 136 so that sealing membrane 148 faces towards puncture lances 138. In the illustrated embodiment, the elongate central neck 184 of perforator assembly 180 (described below) has a generally cylindrical shape, and is received within a central aperture 149 (FIG. 5) of gas release cell 134. In the illustrated embodiment, a plurality of axially-extending interior channels 151 are provided on the inside surface of gas release cell 134, to assist in preventing formation of an airtight seal between the central aperture 149 of gas release cell 134 and the cylindrical elongate central neck 184 of perforator assembly 180. In some embodiments, interior channels 151 are omitted. For example, in some embodiments, the tolerance between the inside surface of shell 146 and the elongate central neck 184 of perforator assembly 180 is sufficient to prevent the formation of an airtight seal between central aperture 149 of gas release cell 134 and elongate central neck 184.

Needle membrane 156 optionally assists in the sealing of gas release chamber 136 to prevent the escape of compressed propellant when gas release cell 134 is ruptured. In some embodiments, the sealing between the components that define gas release chamber 136 is sufficiently tight to generally seal gas release chamber 136 and facilitate retraction of needle 122 without the need for additional sealing components such as needle membrane 156.

In the illustrated embodiment, needle header 132 is retained in place against the distal force applied by a user during the injection phase (an "injection force") by an engagement ring 160. Engagement ring 160 has a central opening 162 (FIG. 5) through which needle 122 passes. In some embodiments, central opening 162 is cylindrically shaped. Engagement ring 160 is frictionally but slidably engaged with the interior surface 144 of syringe barrel 126. Engagement ring 160 is axially slidable within barrel 126 in response to the application of a post-injection force, but is retained in place within barrel 126 during the application of an injection force. Engagement ring 160 is also retained in place within barrel 126 during the application of a force in the proximal direction required to load medicament into medicament chamber 130 (i.e. a loading force).

In some embodiments, engagement ring 160 is frictionally secured in syringe barrel 126. Engagement ring 160 could be secured in place in any suitable manner that is sufficiently strong to retain engagement ring 160 in place during the application of an injection or loading force, but releasable in response to the application of a post-injection force. For example, engagement ring 160 could be held in place by breakable tabs or weakly secured with an adhesive. In the illustrated embodiment, engagement ring 160 assists in puncturing gas release cell 134 in response to the application of a post-injection force, as described below.

Engagement ring 160 allows needle header 132 (and thus needle 122) to move proximally into syringe 124 (within retraction lumen 129) when gas release cell 134 is ruptured. Needle header 132 is also secured with engagement ring 160 in a manner that is sufficiently strong to ensure that needle header 132 does not separate from engagement ring 160 until after the rupture of gas release cell 134. For example, some loading force may be exerted against needle header 132 in the proximal direction when medicament is being loaded into syringe 124, and an injection force will be applied against needle header 132 in the distal direction when the medicament is injected. The engagement between needle header 132 and engagement ring 160 should be sufficiently strong so as not to separate during the application of a loading force in the proximal direction, but sufficiently weak that needle header 132 can separate from engagement ring 160 when gas release cell 134 is ruptured. Needle header 132 can be secured to engagement ring 160 in any suitable manner that provides such a releasable engagement, such as by sufficiently strong friction fit, sufficiently weak adhesive to allow release when gas release cell 134 is ruptured, easily frangible connectors, easily releasable connectors, or the like. In the illustrated embodiment, needle header 132 is secured within engagement ring 160 by a compression fit. In some embodiments, needle header 132 is sized to be of sufficiently large diameter that needle header 132 cannot physically pass through engagement ring 160 in the distal direction.

In some embodiments, plunger 128 and syringe barrel 126 include a plunger locking feature to retain plunger 128 in a position at or near the distal limit of travel of plunger 128. In the illustrated embodiment, the plunger locking feature is provided by a plunger verge 166 and syringe barrel lock 168 (FIG. 4) which are positioned and configured to allow one-way sliding motion therebetween.

Plunger verge 166 is a radially outwardly extending circumferential protrusion on the outside surface of plunger 128. Syringe barrel lock 168 is a radially inwardly extending circumferential protrusion on the inside surface of syringe barrel 126. Both plunger verge 166 and syringe barrel lock 168 are sized so as not to interfere with the axial sliding motion between plunger 128 and syringe 124. However, plunger verge 166 and syringe barrel lock 168 are dimensioned and positioned so that after plunger verge 166 has been slid distally past syringe barrel lock 168, plunger verge 166 cannot thereafter be slid in a proximal direction past syringe barrel lock 168. This configuration essentially locks plunger 128 in a position at or near its distal-most point of travel, making it very difficult to separate plunger 128 from syringe 124 after use. This ensures needle 122 remains securely within retraction lumen 129 after use of syringe 124.

To achieve a one-way sliding motion, the distal surface of plunger verge 166 and/or the proximal surface of syringe barrel lock 168 may be angled or otherwise shaped so that plunger verge 166 may be readily slid past syringe barrel lock 168 in the distal direction. That is, plunger verge 166 may have an inclined surface progressively increasing in diameter from its distal-most portion and/or syringe barrel lock 168 may have an inclined surface progressively increasing in diameter from its proximal-most portion. This configuration allows plunger verge 166 to be easily slid past syringe barrel lock 168 in the distal direction. In some embodiments, the proximal surface of plunger verge 166 and the distal surface of syringe barrel lock 168 is flat, i.e. parallel or nearly parallel to a notional radial cross-section of syringe barrel 126, so that plunger verge 166 cannot readily be slid past syringe barrel lock 168 in the proximal direction.

In some embodiments, plunger 128 includes an opening 170 at its proximal end (FIG. 4). Opening 170 receives a removable plunger plug 172 in sealing engagement therein, so that needle 122 can be retained in retraction lumen 129 when needle 122 has been retracted. Plunger plug 172 may facilitate assembly of syringe assembly 121. In some embodiments, after assembly of syringe assembly 121, plunger plug 172 is permanently secured in place, e.g. with a suitable adhesive. In some embodiments, opening 170 is not provided and plunger plug 172 is not used.

In some embodiments, plunger 128 includes an orifice such as vent hole 174 therein (FIG. 3), for example on the proximal or side surface of plunger 128 or through the top of plunger 128. In some embodiments, vent hole 174 may allow release of air from retraction lumen 129 upstream of needle header 132 and needle port seal 131 when needle 122 is retracted. Vent hole 174 should be positioned proximally at or close to the upstream limit of travel of needle port seal 131, to avoid a loss of pressure that could stop the upstream travel of needle 122 before it has been fully retracted as could occur if, for example, vent hole 174 is positioned too far distally of the upstream limit of travel of needle port seal 131. In some embodiments, a vent hole may be provided in plunger plug 172 instead of through plunger 128.

In some embodiments, the fit between plunger plug 172 and opening 170 is sufficiently tight to retain plunger plug 172 within opening 170, but is not airtight, so that air can be released upstream of needle header 132 when needle 122 is retracted.

In some embodiments, plunger 128 includes a plunger end flange 176 to provide a bearing surface for the fingers of a user, e.g. to facilitate withdrawal of plunger 128 from syringe barrel 126 to draw liquid into medicament chamber 130 and/or administration of medicament using syringe assembly 121.

In some embodiments, gas release cell 134 is initially secured within gas release chamber 136 in any suitable manner to minimize the risk that sealing membrane 148 may be prematurely ruptured by rupturing mechanism 138. For example, the outer surface of shell 146 of gas release cell 134 may be frictionally engaged with the inner surface 144 of syringe barrel 126, or with perforator neck 184 (described below), or gas release cell 134 may be initially affixed to engagement ring 160, or perforator neck 184 in any suitable manner, such as by adhesives. In embodiments including the illustrated embodiment in which movement of gas release cell 134 is required to rupture gas release cell 134 upon application of a post-injection force, the adhesives used should be sufficiently weak to allow gas release cell 134 to move upon application of a post-injection force, but sufficiently strong to retain gas release cell 134 in position during application of a loading force or an injection force.

In some embodiments, gas release cell 134 is not specifically secured within gas release chamber 136 in any manner (i.e. gas release cell 134 is free floating), and the material that sealing membrane 148 is made from is sufficiently strong that mere contact with rupturing mechanism 138 (e.g. as might occur during shipping or loading of syringe assembly 121) in the absence of force applied by a user as a post-injection force is not sufficient to rupture gas release cell 134.

The pressure and volume of propellant in gas release cell 134 should be sufficient to ensure that needle 122 is fully retracted within retraction lumen 129 when gas release cell 134 is ruptured. Gas release cells intended for use with a larger volume of syringe may have a larger volume (and thus contain more compressed propellant) than gas release cells intended for use with a smaller volume of syringe. The appropriate pressure and volume of propellant to be included in gas release cell 134 can be determined by one skilled in the art based on the propellant to be used and the anticipated range of temperatures at which syringe assembly 121 will be used.

A mechanism for rupturing sealing membrane 148 of gas release cell 134 in response to a post-injection force is provided within gas release chamber 136. In the illustrated embodiment, a gas release trigger in the form of one or more puncture lances 138 is provided. Puncture lances 138 are secured within syringe barrel 126 in any suitable manner. In the illustrated embodiment, puncture lances 138 are secured to a perforator mount 180 secured at a distal portion of syringe barrel 126. In alternative embodiments, puncture lances 138 are secured directly to the distal end of syringe barrel 126.

Puncture lances 138 could alternatively be mounted to appropriate portions of engagement ring 160, or to the distal end of plunger 128 (with corresponding holes provided through engagement ring 160 to receive the puncture lances), or integrally formed with such components, such that puncture lances 138 are positioned and disposed to be operable to puncture gas release cell 134 in response to application of a post-injection force, as described below. In such embodiments, the orientation of gas release cell 134 would be reversed by 180°, so that sealing membrane 148 is oriented towards puncture lances 138 to facilitate rupture upon application of a post-injection force.

In the illustrated embodiment, six puncture lances are shown. However, any suitable number of puncture lances could be used, for example, two, three, four or more puncture lances.

Figure 5:
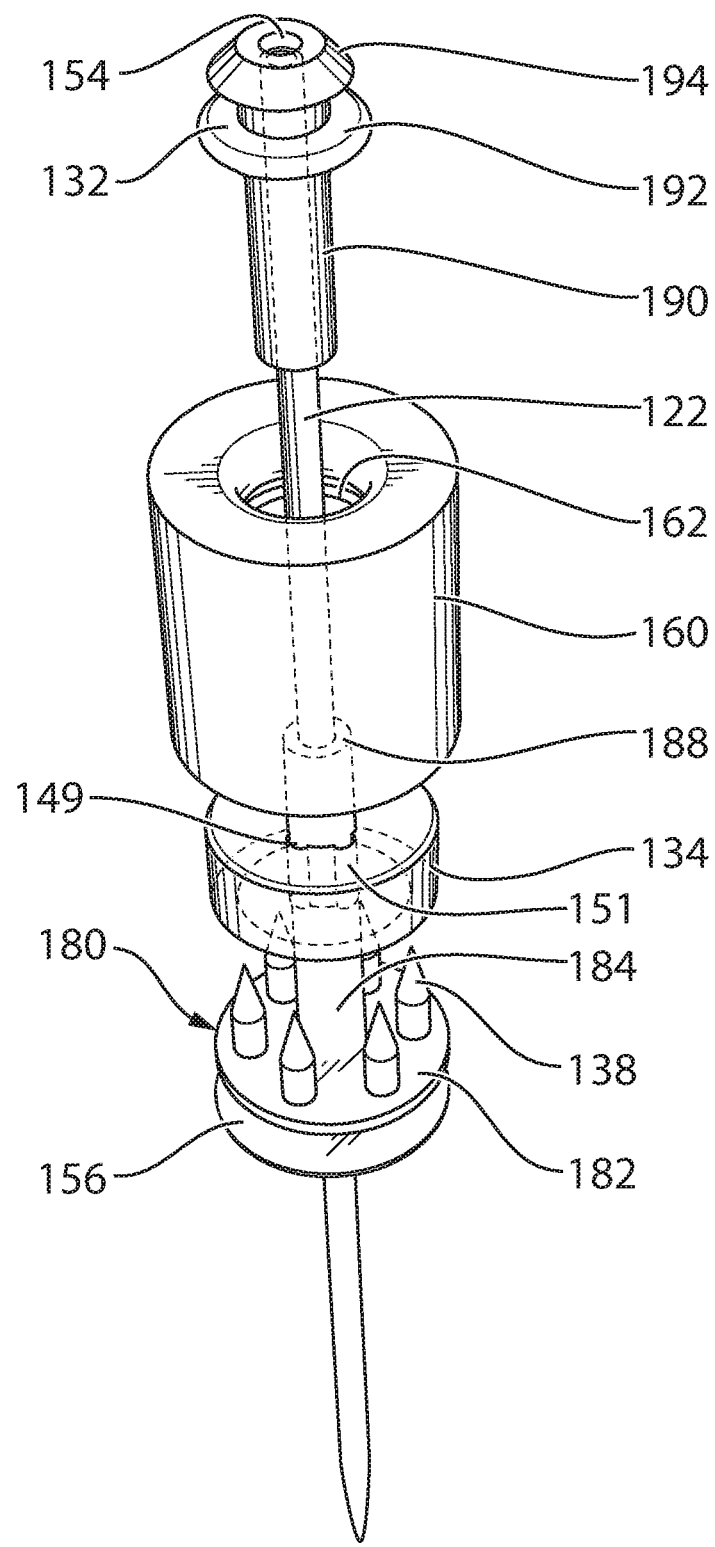
FIG. 5 shows an exploded view of select components of the syringe of FIG. 3.

In the illustrated embodiment, a perforator assembly 180 includes a base 182 on which puncture lances 138 are mounted and an elongate central neck 184 projecting proximally from the base 182. Needle 122 extends through central neck 184. In some embodiments, base 182, puncture lances 138, and central neck 184 may be machined as a single piece, or may be separately manufactured and then joined in any suitable manner, for example by adhesives, welding, or the like. Base 182 may be secured to a perforator mount 186 at the distal end of syringe barrel 126. In some embodiments, the dimensions and materials of base 182 and perforator mount 186 are such that base 182 mates tightly with perforator mount 186, thereby impeding leakage of gases or other fluids from gas release chamber 136. Perforator assembly 180 includes a needle aperture 188 (FIG. 5). In some embodiments, needle aperture 188 is dimensioned to firmly hold needle 122 during the injection phase. In some embodiments, needle aperture 188 sealingly engages with needle 122. In some embodiments, needle membrane 156 is secured to cover needle aperture 188.

In the illustrated embodiment, perforator assembly 180 and engagement ring 160 are axially aligned so that a proximal portion of neck 184 extends within the central opening 162 of engagement ring 160. The distal edge of neck 184 contacts needle header 132. Gas release cell 134 extends around neck 184, as described above.

In the illustrated embodiment as best seen in FIG. 5, needle header 132 has a downstream hollow cylindrical body 190, a collar 192, and an upstream hollow end knob 194. Needle 122 is crimped in, cemented to, or otherwise securely fixed within body 190 of needle header 132. In the illustrated embodiment, needle header 132 is positioned within central opening 162 of engagement ring 160. In some embodiments, needle header 132 is positioned such that knob 194 is approximately flush with the upstream end of engagement ring 160. Hollow cylindrical body 190 of needle header 132 is inserted into central opening 162 of engagement ring 160 on the proximal side thereof. Needle header 132, including collar 192, is inserted within central opening 162 with a fit approaching a snug fit (i.e. a tight fit). Needle header 132 sealingly engages with engagement ring 160 to prevent leakage of medicament or other fluids between needle header 132 and engagement ring 160.

In some embodiments, the proximal tip of needle header 132 is positioned above engagement ring 160, such that hollow end knob 194 projects in the proximal direction from engagement ring 160. In such embodiments, corresponding adjustments can be made to recess needle port seal 131 slightly further in the proximal direction within plunger 128. Embodiments wherein needle header 132 is initially positioned within engagement ring 160 as described above may reduce the likelihood that needle header 132 may be accidentally dislodged prior to use, for example due to forces that may be applied in the course of shipping or handling of syringe assembly 121.

Figure 6:
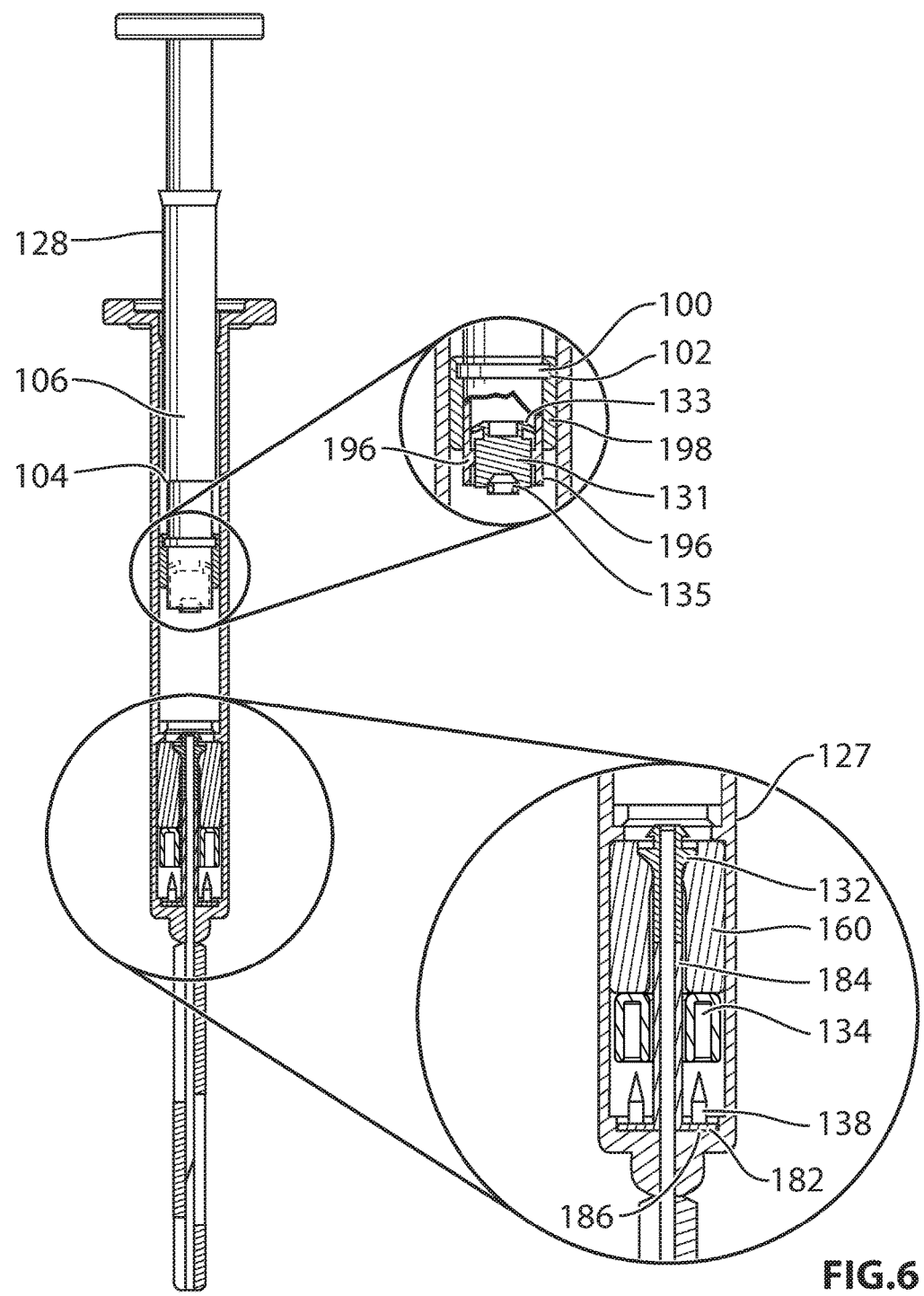
FIG. 6 shows a partial cross-sectional view of the syringe of FIG. 3 in the assembled configuration.

To facilitate retraction of needle 122, plunger 128 includes a narrowed distal plunger neck 196 (FIG. 6). Narrowed distal plunger neck 196 includes at its distal end a needle port seal 131. Needle port seal 131 is frictionally and sealingly engaged within the inner surface of distal plunger neck 196 with a snug fit that prevents movement of needle port seal 131 in response to a loading force or an injection force, but that permits movement of needle port seal 131 in the proximal direction within retraction lumen 129 under pressure applied by the rupture of gas release cell 134. Needle port seal 131 also prevents medicament from entering retraction lumen 129 when syringe assembly 121 is in use.

In some embodiments, needle port seal 131 is positioned within distal plunger neck 196 so that needle port seal 131 engages with needle header 132 at or just before the end of the application of an injection force by a user, or at the start of the application of a post-injection force to plunger 128 by a user. In the illustrated embodiment, needle port seal 131 is mounted within distal plunger neck 196 so that the distal end of needle port seal 131 is flush with the distal portion of distal plunger neck 196. Needle port seal 131 is shaped and configured to engage with needle header 132 without being obstructed by engagement ring 160. In the illustrated embodiment, needle port seal 131 includes a grasping ledge 135 that extends radially inwardly from the distal end of needle port seal to grasp knob 194 of needle header 132.

The diameter of the outer portion of needle port seal 131 is selected so that needle port seal 131 frictionally engages the inner surface of distal plunger neck 196 and of retraction lumen 129. In some embodiments, at least the outermost circumferential portion of needle port seal 131 that engages with these surfaces is made from resilient material, so that needle port seal 131 can expand in diameter to fill the full cross-section of retraction lumen 129 during retraction of needle 122. In the illustrated embodiment, needle port seal 131 includes a sealing portion 133 made from a resilient material that sealingly engages with the walls of retraction lumen 129 to facilitate gas-driven retraction of needle 122.

In some embodiments, retraction lumen 129 is tapered, such that the proximal portion of retraction lumen 129 has a larger diameter than the distal portion of retraction lumen 129. In such embodiments, the resilient outermost circumferential portion of needle port seal 131 expands as needle port seal 131 moves proximally within retraction lumen 129, to maintain sealing engagement within retraction lumen 129.

To facilitate injection of medicament from medicament chamber 130, in the illustrated embodiment a hollow deformable plunger seal 198 is provided on plunger 128. Plunger seal 198 surrounds distal plunger neck 196 with a tight fit.

In some embodiments, plunger seal 198 is constrained from axial movement during normal use of syringe assembly 121 by engagement of a radially outwardly extending collar 100 on distal plunger neck 196 with an annular recess 102 formed on the inside surface of plunger seal 198, or in any other suitable manner. The fit, dimensions and material used for plunger seal 198 are selected so that plunger seal 198 slidingly but sealingly engages the inner wall of barrel 126 with some resistance.

Internal radial wall 127 defines an opening that is dimensioned so that distal plunger neck 196 can pass therethrough, but so that plunger seal 198 cannot. Thus, movement of plunger seal 198 in the distal direction is stopped when seal 198 abuttingly engages radial wall 127. Application of a post-injection force thus causes distal plunger neck 196 to move in the distal direction, while plunger seal 198 is forced slidingly in the proximal direction (relative to plunger neck 196) along distal plunger neck 196. In the illustrated embodiment, engagement of plunger seal 198 with a radially extending shoulder 104 (FIG. 6) formed where the main body 106 of plunger 128 meets distal plunger neck 196 prevents further movement of plunger seal 198 in the proximal direction relative to plunger 128 after the post-injection force has been applied.

In use, needle cover 150 may be twisted off or otherwise removed in any suitable manner to expose needle 122. Downstream force is applied by a user to the upstream plunger end flange 125 and/or to plunger plug 172 to eject air out of medicament chamber 130, if necessary. When nearly all of the air has been forced out of medicament chamber 130, but before plunger verge 166 engages with syringe barrel lock 168, the tip 152 of needle 122 can be submerged in liquid medicament contained in a supply vial, which may be of a conventional type.

Medicament or other liquid for injection is drawn into medicament chamber 130 by withdrawing plunger 128 proximally relative to syringe barrel 126 in the same manner as a conventional syringe. After medicament chamber 130 has been filled with the desired volume of medicament, air may be removed in the conventional manner by inverting syringe assembly 121 so that needle 122 is pointing upwardly, tapping syringe 124 to displace any air therewithin and allowing the air to float above the medicament, and applying a distally-directed force to the plunger 128 so that residual air is forced out through needle 122.

Needle 122 is positioned at an injection site of a subject in the conventional manner. Medicament can be discharged from chamber 130 by applying a distally-directed force on plunger end flange 176 and/or plunger plug 172 in a conventional manner, thus causing plunger seal 198 to exert a distal biasing pressure on the medicament contained in chamber 130. The distally-directed biasing pressure is sufficient to force medicament through needle 122. However, the pressure is not sufficient to overcome the frictional force securing engagement ring 160 to the inner surface of syringe barrel 126, nor is the corresponding upstream pressure on the tip of plunger 128 sufficient to overcome the frictional force between needle carrier 131 and distal plunger neck 196.

Figure 7:
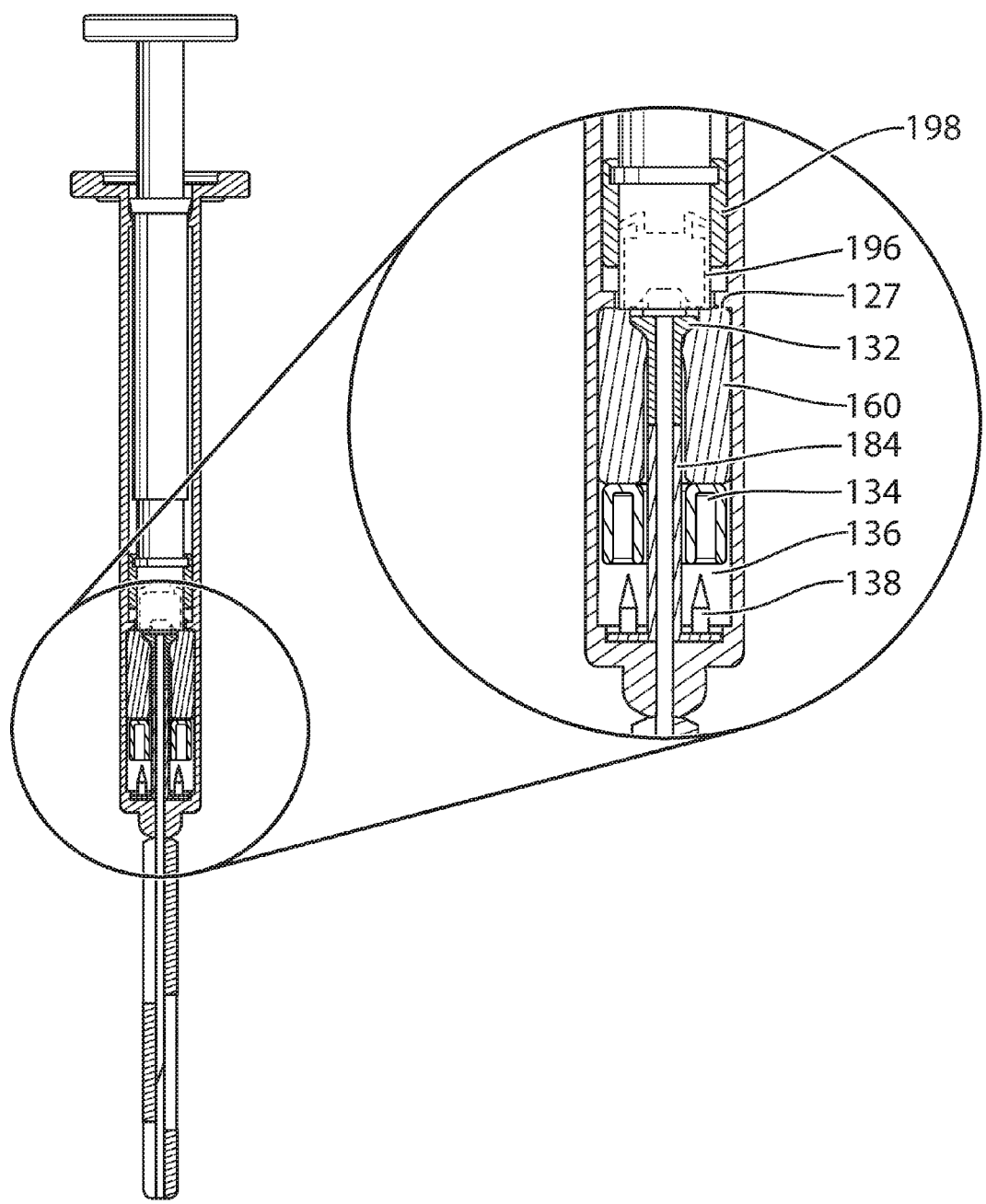
FIG. 7 shows a partial cross-sectional view of the syringe of FIG. 3 at the end of the injection stroke.
Figure 8:
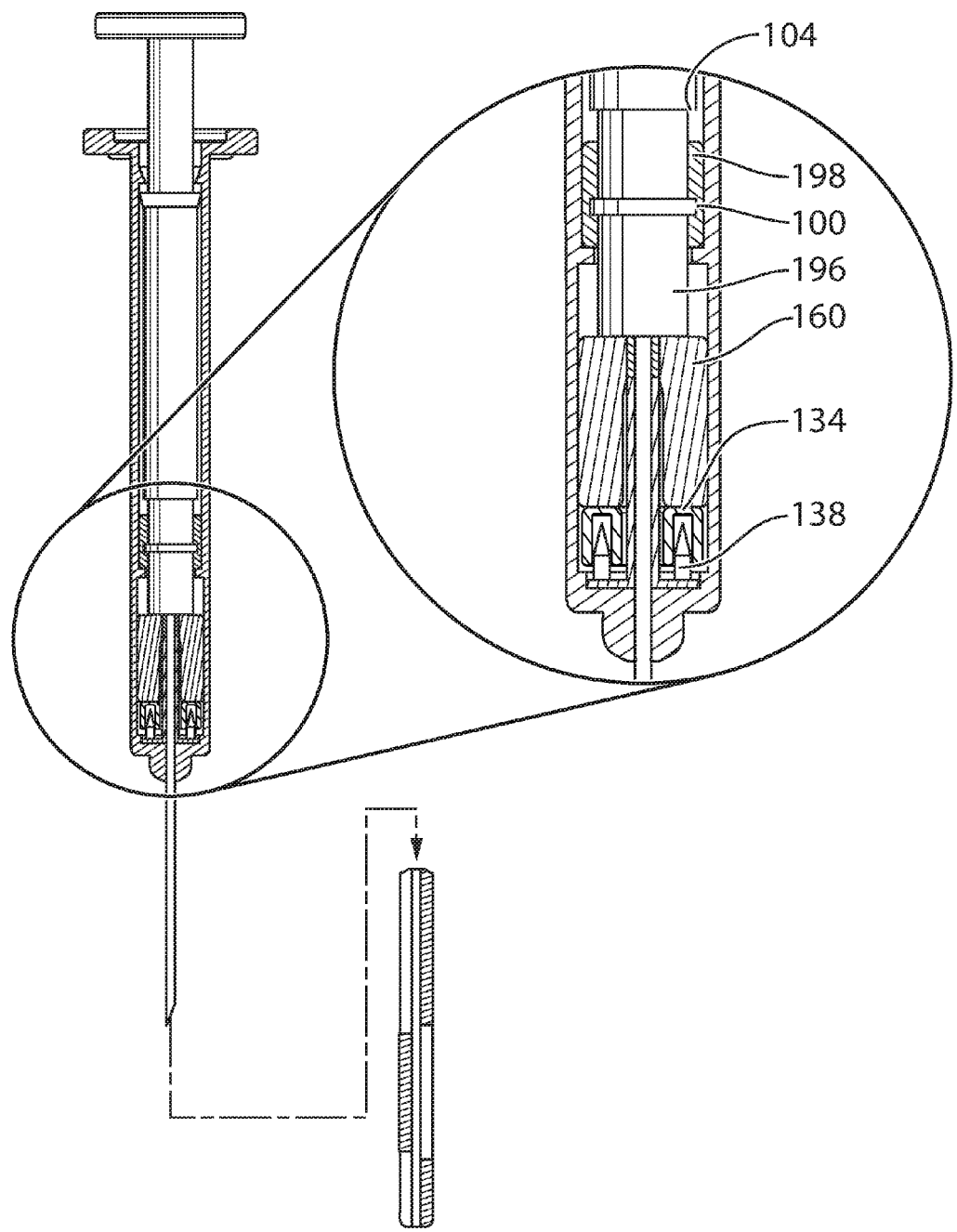
FIG. 8 shows a partial cross-sectional view of the syringe of FIG. 3 during the application of a post-injection force by a user.

With reference to FIGS. 7 and 8, after all or substantially all of the medicament has been injected into a subject, a user continues to apply force, now a post-injection force, in the distal direction against plunger 128. Movement of distal plunger neck 196 in the distal direction past internal radial wall 127 causes distal plunger neck 196 to impinge on engagement ring 160. Needle port seal 131 is forced onto hollow end knob 194 of needle header 132, thereby sealing needle header 132 so that no medicament or other fluids may be passed through needle 122. Engagement of needle port seal 131 with hollow end knob 194 forms needle retraction assembly 108 (shown in dotted outline in the retracted position in FIG. 9), which includes needle port seal 131, needle header 132, and needle 122. Further motion of plunger seal 198 in the distal direction is prevented by internal radial wall 127.

Engagement of needle header 132 with central neck 184 of perforator assembly 180 prevents movement of needle retraction assembly 108 in the distal direction. Continued application of a post-injection force causes distal plunger neck 196 to move axially past internal radial wall 127 and to impinge on engagement ring 160. The post-injection force overcomes the frictional engagement between engagement ring 160 and the interior surface of syringe barrel 126, causing engagement ring 160 to move in the distal direction (FIG. 8). Continued motion of engagement ring 160 also forces gas release cell 134 in the distal direction, causing gas release cell 134 to impinge on puncture lances 138. Gas release cell 134 is ruptured, thereby releasing propellant into gas release chamber 136.

Figure 9:
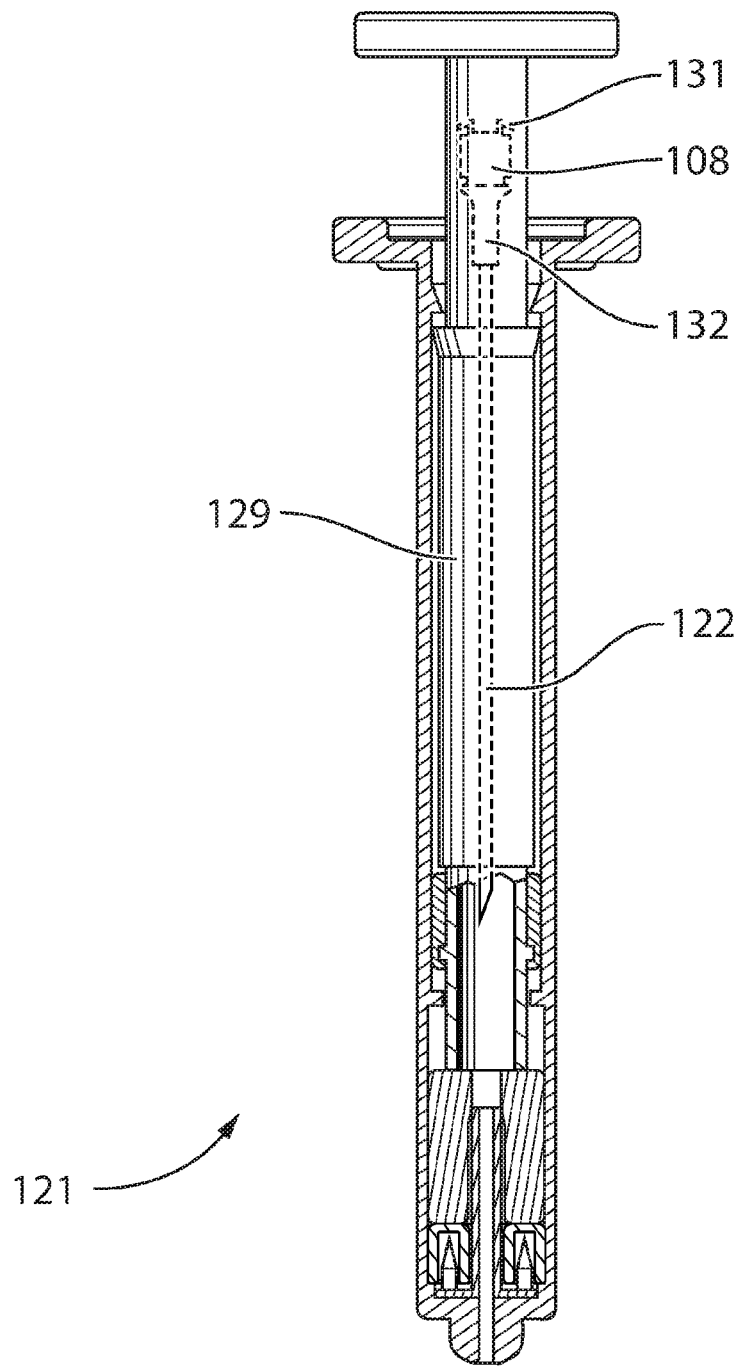
FIG. 9 shows a partial cross-sectional view of the syringe of FIG. 3 in the retracted position.

The released propellant remains under pressure within the confines of the gas release chamber 136, and therefore a proximal force is applied against needle retraction assembly 108. In embodiments in which the compressed propellant comprises a liquid phase, the propellant will transition to the gas phase when gas release cell 134 is ruptured. The proximal force applied by the released gas is sufficiently strong to overcome the frictional force securing the needle header 132 within the central opening 162 of engagement ring 160, and also to overcome the frictional force securing needle port seal 131 within distal plunger neck 196. The proximally-directed biasing pressure causes needle retraction assembly 108 to slide proximally into retraction lumen 129, thus retracting needle 122 inside retraction lumen 129 (FIG. 9). The volume and pressure of propellant in gas release cell 134 should be sufficient to retract the full length of needle 122 inside retraction lumen 129.

Suitable materials for the manufacture of syringe assembly 121 may be selected by one skilled in the art. For example, syringe barrel 126 and plunger 128 may be made from a plastic material, such as appropriate polymers, homopolymers or copolymers. Plunger seal 198 may be made from any suitable material, for example elastomers or rubber. In some embodiments, plunger seal 198 may be a self-lubricating seal. In some embodiments, syringe barrel 126 and/or plunger seal 198 may be treated with a medical grade lubricant. Needle 122 may be made of medical grade needle tubing. The compressed propellant used in gas release cell 134 may be any suitable propellant, for example a pharmaceutical-grade hydrofluorocarbon such as 1,1,1,2-tetrafluoroethane or medical-grade nitrogen. Suitable materials for manufacture of gas release cell 134 include suitable polymers such as, for example, nylon, polyethylene, polypropylene, polystyrene or the like, or suitable copolymers thereof. Components may be sterilized prior to packaging in any suitable manner, for example with e-beam radiation, γ-radiation, or ethylene oxide (EtO) gas. The materials selected for manufacture of syringe assembly 121 should be compatible with the medicament to be administered to the subject.

In some embodiments, syringe 124 is a prefilled syringe, i.e. syringe 124 has been filled with a predetermined quantity of a specified medicament. In use, prefilled syringe 124 does not need to be loaded with medicament, but can simply be used to inject the medicament already contained therein in a subject in the manner described above.

While the exemplary embodiment of a pneumatically-actuated retractable-needle syringe incorporating gas release cell 134 described above is similar to that described in U.S. Pat. No. 7,811,259 to Klippenstein, embodiments of the present invention include gas release cells suitable for use in syringes similar to those described in U.S. Pat. No. 5,868,713, or modular gas-actuated retractable-needle assemblies such as those described in Patent Cooperation Treaty application No. PCT/CA2012/050184 filed 26 Mar. 2012, the entirety of which is hereby incorporated herein by reference.

While a number of exemplary aspects and embodiments have been discussed above, those of skill in the art will recognize certain modifications, permutations, additions and sub-combinations thereof. Without limitation, such modifications may include:

While inner and outer walls of the shell of the gas release cell have been described as being made of rigid material, in some embodiments the base of the gas release cell need not be made from a rigid material.

The relative orientation of puncture lances 138 and gas release cell 134 could be reversed, so that puncture lances 138 are provided on the distal side of engagement ring 160.

The shape of the gas release cell could be modified based on the desired application. For example, while gas release cell 30 has been described as generally cylindrical in shape, for example to fit within the generally cylindrical barrel of a hypodermic syringe, other shapes are possible. For example, the gas release cell could be provided with a square rather than circular cross-section if it was desired to use the gas release cell within a component having a square-shaped cross-section.

Accordingly, the scope of the claims should not be limited by the preferred embodiments set forth in the description, but should be given the broadest interpretation consistent with the specification as a whole.

What is claimed is:

1. A gas release cell for use with a pneumatically-actuated sharps-containing medical device, the gas release cell comprising;
   an inner wall comprising a rigid material, the inner wall defining an aperture through the gas release cell;
   an outer wall comprising a rigid material extending around the inner wall;
   a base coupled to the inner and outer walls and in sealing engagement therewith;
   a separate rupturable membrane coupled to the inner and outer walls and in sealing engagement therewith, so that the rupturable membrane, inner and outer walls and base define a sealed propellant chamber; and
   compressed propellant contained within the propellant chamber.

2. A gas release cell as defined in claim 1, wherein the base is integrally formed with the inner wall and the outer wall.

3. A gas release cell as defined in claim 1, wherein the inner wall is cylindrical in shape; wherein the outer wall is cylindrical in shape; and wherein the inner wall and the outer wall are in axial alignment.

4. A gas release cell as defined in claim 1, wherein the gas release cell is toroidal in shape.

5. A gas release cell as defined in claim 1, wherein the base is coupled to a first end of the inner wall and to a first end of the outer wall.

6. A gas release cell as defined in claim 5, wherein the rupturable membrane is coupled to a second end of the inner wall and to a second end of the outer wall.

7. A gas release cell as defined in claim 1, wherein a surface of the inner wall or of the outer wall that is coupled to the rupturable membrane comprises a curved radius.

8. A gas release cell as defined in claim 1, wherein a surface of the inner wall or of the outer wall that is coupled to the rupturable membrane comprises a flat surface.

9. A gas release cell as defined in claim 1, comprising surface features for preventing formation of a seal between the gas release cell and one or more adjacent components of a medical device in which the gas release cell is used.

10. A gas release cell as defined in claim 9, wherein the surface features comprise axially-extending ribs formed on an interior circumference or on an exterior circumference of the gas release cell.

11. A gas release cell as defined in claim 9, wherein the surface features comprise axially-extending, channels formed on an interior circumference or on an exterior circumference of the gas release cell.

12. A gas release cell as defined in claim 9, wherein the surface features firm a cross-sectional shape of the inner wall or of the outer wall that provides a gas passage between the gas release cell and the one or more adjacent components of the medical device in which the gas release cell is to be used.

13. A gas release cell as defined in claim 12, wherein the one or more adjacent components of the medical device comprise a generally cylindrical shape.

14. A gas release cell as defined in claim 1, wherein the inner wall, the outer wall, and the base, comprise a polymer, a homopolymer or a co-polymer.

15. A gas release cell as defined in claim 14, wherein the inner wall, the outer wall, and the base comprise a multi-layer film, wherein the multi-layer film comprises a laminate, wherein the laminate comprises the polymer, the homopolymer or the co-polymer, or multiple layers thereof, and a metal foil.

16. A gas release cell as defined in claim 1, wherein the inner and outer walls and the base are integrally formed by extrusion, injection molding or compression molding.

17. A gas release cell as defined in claim 1, wherein the rupturable membrane comprises a polymer, a homopolymer or a co-polymer.

18. A gas release cell as defined in claim 17, wherein the rupturable membrane comprises a multi-layer film, wherein the multi-layer film comprises a laminate, wherein the laminate comprises the polymer, the homopolymer or the co-polymer, or multiple layers thereof, and a metal foil.

19. A gas release cell as defined in claim 17, wherein the inner wall, the outer wall and the base comprise the same polymer, the same homopolymer or the same co-polymer as the rupturable membrane.

20. A gas release cell as defined in claim 1, wherein the propellant comprises medical grade nitrogen or carbon dioxide.

* * * * *